United States Patent
Arendash

(10) Patent No.: US 12,318,624 B2
(45) Date of Patent: Jun. 3, 2025

(54) BRAIN IMMUNOREGULATION THROUGH TRANSCRANIAL ELECTROMAGNETIC TREATMENT

(71) Applicant: NeuroEM Therapeutics, Inc., Phoenix, AZ (US)

(72) Inventor: Gary W. Arendash, Phoenix, AZ (US)

(73) Assignee: NeuroEM Therapeutics, Inc., Tampa Bay, FL (US)

( * ) Notice: Subject to any disclaimer, the term of this patent is extended or adjusted under 35 U.S.C. 154(b) by 0 days.

(21) Appl. No.: 17/508,727

(22) Filed: Oct. 22, 2021

(65) Prior Publication Data

US 2022/0040492 A1 Feb. 10, 2022

Related U.S. Application Data

(63) Continuation-in-part of application No. 16/359,749, filed on Mar. 20, 2019, now Pat. No. 11,813,472, and
(Continued)

(51) Int. Cl.
*A61N 2/02* (2006.01)
*A61N 1/04* (2006.01)
(Continued)

(52) U.S. Cl.
CPC ............. *A61N 2/02* (2013.01); *A61N 1/0476* (2013.01); *A61N 1/36025* (2013.01); *A61N 1/40* (2013.01); *A61N 2/004* (2013.01)

(58) Field of Classification Search
CPC .... A61N 1/0476; A61N 1/36025; A61N 1/40; A61N 2/004; A61N 2/006; A61N 2/02;
(Continued)

(56) References Cited

U.S. PATENT DOCUMENTS 6,248,126 B1 6/2001 Lesser
6,334,069 B1 12/2001 George
(Continued)

FOREIGN PATENT DOCUMENTS

EP 1907052 1/2010
EP 1606010 B1 2/2012
(Continued)

OTHER PUBLICATIONS

Spring, K. R., Inoue, S., Flynn, B. O., Sutter, R. T., & Davidson, M. W. (n.d.). Electromagnetic wave propagation. Electromagnetic Wave Propagation—Java Tutorial | Olympus LS. https://www.olympus-lifescience.com/en/microscope-resource/primer/java/polarizedlight/emwave/.*
(Continued)

*Primary Examiner* — Paula J Stice
(74) *Attorney, Agent, or Firm* — Bamert Regan PLLC

(57) ABSTRACT

The present disclosure describes a method of regulating (re-balancing) the brain's immune system. According to the method, an array of electromagnetic emitters are positioned proximal to the subject. An electromagnetic wave generator generates electromagnetic waves at a predetermined set of parameters. In an example of the emitters positioned proximal to the subject's head, the brain's immune function is normalized/rebalanced in an area under the electromagnetic emitters by applying the electromagnetic waves to the subject through the electromagnetic emitters. With either head or body placement of emitters, a rebalancing of the brain's cytokines/immune mediators occurs.

17 Claims, 12 Drawing Sheets

Related U.S. Application Data a continuation-in-part of application No. 16/273,519, filed on Feb. 12, 2019, now Pat. No. 11,752,356, and a continuation-in-part of application No. 16/865,250, filed on May 1, 2020, now Pat. No. 11,759,650, which is a continuation-in-part of application No. 14/205,333, filed on Mar. 11, 2014, now Pat. No. 10,765,879.

(60) Provisional application No. 61/776,097, filed on Mar. 11, 2013.

(51) Int. Cl.
  *A61N 1/36* (2006.01)
  *A61N 1/40* (2006.01)
  *A61N 2/00* (2006.01)

(58) Field of Classification Search
  CPC ...... A61N 5/02; A61B 5/4082; A61B 5/4088; A61B 5/4836; A61B 5/4848; A61B 5/6803; A61B 5/6844
  USPC ........................................................ 607/154
  See application file for complete search history.

(56) References Cited

U.S. PATENT DOCUMENTS

| | | |
|---|---|---|
| 6,410,137 B1 | 6/2002 | Bunyan |
| 6,463,336 B1 | 10/2002 | Mawhinney |
| 6,876,337 B2 | 4/2005 | Larry |
| 7,672,648 B1 | 3/2010 | Groe |
| 8,684,901 B1 | 4/2014 | Zabara |
| 8,868,177 B2 | 10/2014 | Simon et al. |
| 9,672,393 B1 | 6/2017 | Zhu |
| 10,765,879 B2 * | 9/2020 | Arendash ............... A61N 1/40 |
| 10,792,483 B2 | 10/2020 | Andocs |
| 10,850,096 B2 | 12/2020 | Teng |
| 11,058,886 B1 | 7/2021 | Matloubian |
| 11,229,788 B1 | 1/2022 | John |
| 2004/0122281 A1 | 6/2004 | Fischell |
| 2004/0127895 A1 | 7/2004 | Flock |
| 2004/0176805 A1 | 9/2004 | Whelan |
| 2004/0181115 A1 | 9/2004 | Sandyk |
| 2004/0199070 A1 | 10/2004 | Krockel |
| 2005/0228209 A1 | 10/2005 | Schneider |
| 2007/0244530 A1 | 10/2007 | Ren |
| 2007/0249959 A1 * | 10/2007 | Kiefer ..................... A61N 2/004 600/559 |
| 2008/0269851 A1 | 10/2008 | Deem |
| 2009/0131739 A1 | 5/2009 | Shalev |
| 2009/0156884 A1 | 6/2009 | Schneider |
| 2009/0276019 A1 | 11/2009 | Perez |
| 2010/0042168 A1 | 2/2010 | Pasche |
| 2010/0114086 A1 | 5/2010 | Deem |
| 2010/0210894 A1 | 8/2010 | Pascual-Leone |
| 2011/0230701 A1 | 9/2011 | Simon |
| 2012/0065456 A1 | 3/2012 | Arendash |
| 2012/0089201 A1 | 4/2012 | Pilla |
| 2012/0116149 A1 * | 5/2012 | Pilla .................... A61N 1/36025 600/14 |
| 2012/0172954 A1 | 7/2012 | Zastrow |
| 2012/0289869 A1 | 11/2012 | Tyler |
| 2013/0237742 A1 | 9/2013 | Capstick |
| 2014/0187851 A1 | 7/2014 | Cetroni |
| 2014/0228620 A1 | 8/2014 | Vasishta et al. |
| 2014/0303425 A1 * | 10/2014 | Pilla ....................... A61B 6/037 600/15 |
| 2014/0330353 A1 | 11/2014 | Knight |
| 2015/0209566 A1 | 7/2015 | Peyman |
| 2015/0342661 A1 | 12/2015 | Ron Edoute |
| 2016/0022976 A1 * | 1/2016 | Peyman ............. A61K 47/6929 600/407 |
| 2017/0014637 A1 | 1/2017 | Basser |
| 2017/0065326 A1 | 3/2017 | Rosen |
| 2017/0209579 A1 | 7/2017 | Curley |
| 2019/0030354 A1 | 1/2019 | Turner |
| 2019/0255344 A1 * | 8/2019 | Carter ................ A61N 1/36034 |
| 2019/0290355 A1 | 9/2019 | Amos |
| 2020/0038509 A1 | 2/2020 | Corr |
| 2020/0078600 A1 | 3/2020 | Dinh |
| 2020/0164195 A1 | 5/2020 | Lowsky |
| 2020/0297286 A1 | 9/2020 | Costa |
| 2020/0346028 A1 | 11/2020 | Neuroem |
| 2021/0153925 A1 | 5/2021 | Kim |
| 2021/0177491 A1 | 6/2021 | Onik |
| 2021/0220480 A1 | 7/2021 | Peyman |
| 2021/0338265 A1 | 11/2021 | Cohn |

FOREIGN PATENT DOCUMENTS

| | | |
|---|---|---|
| EP | 2414038 | 8/2012 |
| WO | 2007044386 | 4/2007 |
| WO | 2008008545 A3 | 9/2008 |
| WO | 2008141296 | 11/2008 |
| WO | 2017157874 A1 | 9/2017 |
| WO | 2020102312 A1 | 5/2020 |
| WO | 2020141527 A1 | 7/2020 |
| WO | 2020180653 A1 | 9/2020 |

OTHER PUBLICATIONS

Arendash; "Transcranial Electromagnetic Treatment Against Alzheimer's Disease: Why it has the Potential to Trump Alzheimer's Disease Drug Development," Journal of Alzheimer's Disease, 32 (Jun. 2012) pp. 243-266.

Nguyen, et al; "The Effect of a High Frequency Electromagnetic Field in the Microwave Range on Red Blood Cells"; Sep. 7, 2017.

Karsten, et al; "Red Blood Cells are Dynamic Reservoirs of Cytokines"; Feb. 15, 2018.

Arendash; A Clinical Trial of Transcranial Electromagnetic Treatment in Alzheimer's Disease: Cognitive Enhancement and Associated Changes in Cerebrospinal Fluid, Blood, and Brain Imaging; Journal of Alzheimer's Disease 71 (2019) pp. 57-82.

Arendash; Review of the Evidence that Transcranial Electromagnetic Will Be a Safe and Effective Therapeutic Against Alzheimer's Disease; Journal of Alzheimer's Disease 53 (2016) pp. 753-771.

Rasouli; "Attenuation of interleukin-1beta by pulsed electromagnetic fields after traumatic brain injury"; Neuroscience Letters 519 (2012) 4-8.

Merighi; "Signaling pathways involved in anti-inflammatory effects of Pulsed Electromagnetic Field in microglial cells"; Cytokine 125 (2020) 154777.

Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.

Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.

Gerstner Elizabeth R. et al., AntiEndothelial Growth Factor Therapy for Malignant Glioma, Curr Neurol Neurosci Rep. May 2009, 9(3):254-262, p. 2, paragraphs 2-3.

* cited by examiner

US 12,318,624 B2

BRAIN IMMUNOREGULATION THROUGH TRANSCRANIAL ELECTROMAGNETIC TREATMENT

RELATED APPLICATIONS

The present application claims benefit to and is a continuation-in-part of U.S. application Ser. No. 16/865,250, filed May 1, 2020, which is a continuation-in-part of U.S. application Ser. No. 14/205,333, filed Mar. 11, 2014, which claims the benefit of U.S. Provisional Application No. 61/776,097, filed Mar. 11, 2013. The present application also claims benefit to and is a continuation-in-part of U.S. application Ser. No. 16/273,519, filed Feb. 12, 2019. The present application also claims benefit to and is a continuation-in-part of U.S. application Ser. No. 16/359,749, filed Mar. 20, 2019. These applications are incorporated herein by reference in their entireties.

BACKGROUND OF INVENTION

There are many human "age-related" diseases that are accompanied by and involve dysregulation of the immune system. This immune dysregulation or imbalance can be a significant component to the disease process and symptoms, or a primary response of the body to the disease. Moreover, immune dysfunction associated with various diseases can affect not only peripheral tissues (e.g., rheumatoid arthritis, cancers, cardiovascular disease), but can also affect the brain (e.g., Alzheimer's Disease, Parkinson's Disease). Regarding immune regulation in both the body and the brain, cytokines are the immune system's "modulators" or "effectors". In the brain particularly, there are multiple cells that secrete cytokines to influence brain function—microglia, astrocytes, choroid plexus epithelial cells, and even neurons to some extent.

A substantial part of aging and the diseases that accompany aging can be explained by an imbalance between "pro-inflammatory" cytokines and "anti-inflammatory" cytokines in the brain and/or the body. This imbalance occurs during aging and involves a low-grade, chronic, and progressive prominence of pro-inflammatory cytokines over anti-inflammatory cytokines that is often referred to as "inflamm-aging". The resulting immunosenescence (e.g., a process of immune dysfunction that occurs with age) appears to be the main factor for mortality in the aged population. Along this line, humans who live past 100 years (centenarians) have a robust presence of pro-inflammatory cytokines in their blood. However, they also have a high level of anti-inflammatory cytokines, which balance the pro-inflammatory cytokines. Such a vibrant re-balancing of the immune system in older age to the balance typical of middle age would thus lessen occurrence of age-related diseases and increase life span.

BRIEF DESCRIPTION OF THE DRAWINGS

The accompanying drawings illustrate various examples of the principles described herein and are a part of the specification. The illustrated examples do not limit the scope of the claims.

Figure 1:
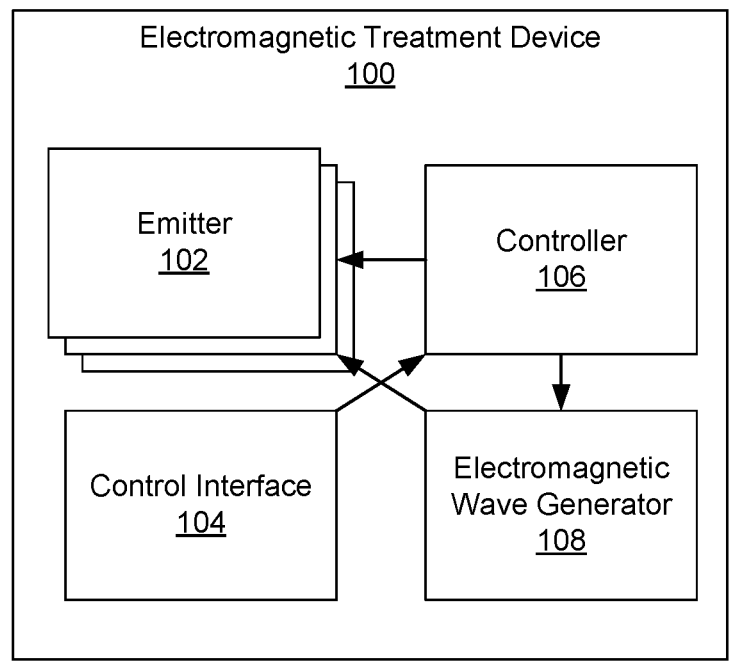
FIG. 1 is a block diagram of an electromagnetic treatment device, according to an example of the principles described herein.

The presented figures provide examples and/or implementations consistent with the methods described in this provisional application. However, the description is not limited to the examples and/or implementations shown in the figures.

DETAILED DESCRIPTION OF THE INVENTION

Cytokine dysregulation is believed to play a key role in remodeling of the immune system in older age. More specifically, there is an increasing, age-related inability to maintain balance between the immune system's pro-inflammatory and anti-inflammatory components. Thus, as one ages, there is a progressive weighing toward pro-inflammatory cytokines called "inflamm-aging". This low-level, chronic state of inflammation in brain and body appears to be a key and common element to most age-related diseases, including Alzheimer's Disease, cancer, and cardiovascular disease.

If inflamm-aging is the key to understanding age-related diseases, a therapeutic intervention that could rebalance numerous cytokines (pro- and anti-inflammatory) in the brain and/or body's immune system would stand to be a viable pathway to healthy aging and longevity. Unfortunately, there is no drug, biologic, device, or methodology that can re-balance the body and brain's immune system in older age. This would be a major undertaking for any therapeutic intervention in that both a maintenance/increase in pro-inflammatory cytokines and an enhancement in anti-inflammatory cytokines would be necessary in brain and body to comprehensively rebalance cytokines back to the levels in young- or middle-aged adults. It is noteworthy that, although the recently-discovered meningeal lymphatic system of the brain provides a linkage between the brain and body immune components, there remains no therapeutic intervention that has the capacity to regulate/rebalance the cytokine/immune mediators in either brain or body, much less both of them in sync.

Aside from pharmacologic, biologic, or life-style interventions, "non-pharmacologic" approaches against diseases of aging (such as Alzheimer's Disease (AD)) have emerged and have been clinically tested, or are currently being clinical tested. These "neuromodulatory device" approaches include transcranial magnetic stimulation (tMS), transcranial direct current stimulation (tDCS), and deep brain stimulation (DBS). All three of these approaches stimulate the activity of neurons in the brain. However, as is the case for pharmaceutic and biologic agents, none of these approaches have thus far been shown to be therapeutic against diseases of aging—particularly to stop or reverse the cognitive impairment of AD. Two newer neuromodulatory approaches (transcranial photomodulation and transcranial ultrasound treatment) are only now beginning clinical trials against AD. Collectively or separately, these five neuromodulatory approaches have not been shown to address the brain or body immune system imbalance that characterizes aging and age-related diseases, particularly as defined by imbalanced brain or body levels of pro-inflammatory and anti-inflammatory cytokines.

Thus, it can be concluded from the existing approaches that there is no therapeutic intervention capable of rebalancing the immune system's pro- and anti-inflammatory components during aging, particularly in relation to immunoregulation within the brain and life extension in good health. Indeed, a balanced immune system may be the pathway to life extension/longevity.

Studies involving nonagenarians (90+) and centenarians (100+) suggests that it may be possible to delay or reduce the risk of age-related diseases and that aging itself may be potentially delayed by a rebalancing or normalization of cytokines and/or immune modulators (referred to herein as cytokines/immune mediators) in brain and body. Along this line, many centenarians have both an enhanced pro-inflammatory status and an enhanced anti-inflammatory status. In other words, centenarians have a balanced, robust immune system of pro- and anti-inflammatory components that contribute to their healthy longevity.

A method to regulate cytokines/immune mediators in older age such that both pro- and anti-inflammatory cytokines are vigorous and balanced may prevent or even stabilize/reverse many age-related diseases of brain and body, to result in an increased life span in good health (an increased "healthspan").

Transcranial Electromagnetic Treatment (TEMT) is a promising neuromodulatory approach against diseases of aging, such as AD. Comprehensive pre-clinical studies in AD transgenic mice have shown that TEMT penetrates the brain and its neurons to "disaggregate" small aggregates/oligomers of two toxic proteins that appear to be the root causes of AD. These toxic proteins are Aβ and tau. These actions by TEMT, in combination with its ability to enhance mitochondrial function in neurons, appear to play a key role in the consistent cognitive benefits provided by TEMT in AD transgenic mice.

To translate these findings to clinical trials in human AD subjects, the MEMOREM™ device provides full forebrain treatment with electromagnetic/radiofrequency waves through multiple emitters distributed on the human head surface to induce electromagnetic (EM) fields in the brain. As an example of a device that provides EM fields into the brain, the MEMOREM™ device has been shown to provide considerable cognitive benefit to AD subjects, changes in their Aβ levels within cerebrospinal fluid (CSF) consistent with Aβ disaggregation in the brain, and evidence of enhanced brain function in their functional magnetic resonance imaging (fMRI) scans. Thus, interventions such as the MEMOREM™ device that provide electromagnetic field treatment to the brain could provide significant therapeutic benefits.

The present specification describes the application of electromagnetic field treatment to rebalance immune function in the aging human brain and to increase human longevity. It should be noted that the described methods, systems and results of the present specification were arrived at from "human" studies (not in vitro or animal studies), and, as such, have direct applicability to humans.

Accordingly, the present specification presents methods to: 1) provide immunoregulation in the human brain, as defined by the lowering of high cytokine/immune mediator levels and/or the increasing of low cytokine/immune mediator levels in the brain and/or CSF (referred to herein as "brain/CSF"), and 2) increase human life span, through such immunoregulation or otherwise in the brain and/or body. It should be noted that the first method does not involve the influencing of any blood/plasma components going through the brain or body vasculature. As used herein, the term "brain" may refer to both brain tissue and the cerebrospinal fluid (CSF) in and around the brain. Thus, the term "brain" may refer to brain tissue and/or CSF.

The present specification describes methodologies that can increase life span (longevity) of a subject (e.g., a human), in part by reducing the risk of age-related diseases and thus increasing the chances of healthy, disease-free aging. Specifically, a first method is provided whereby the human brain is treated with electromagnetic fields through Transcranial Electromagnetic Treatment (TEMT). A second method provides electromagnetic fields to the body or periphery through peripheral electromagnetic treatment (PEMT). The use of one or both of these two bioengineering methodologies for increasing life span is described in the present specification.

Turning now to the figures, FIG. 1 is a block diagram of an electromagnetic treatment device (100), according to an example of the principles described herein. Specifically, FIG. 1 depicts an electromagnetic treatment device (100) that includes an array of electromagnetic emitters (102). The electromagnetic emitters (102) may be positioned adjacent a head surface of the subject in, for example, a transcranial electromagnetic treatment (TEMT) device (100). In another example, the electromagnetic emitters (102) are positioned adjacent a body surface of the subject in, for example, a peripheral electromagnetic treatment (PEMT). The electromagnetic emitters (102) project an electromagnetic field toward the head and/or body of the subject (e.g., a patient). The electromagnetic emitter(s) (102) is (are) activated to apply electromagnetic fields/treatment to the subject primarily for the remedy of diseases or conditions of immune system imbalance wherein cytokine levels are abnormally high or low.

In one example, electromagnetic waves may be generated by the electromagnetic wave generator (108), sent to an emitter (102), and then passed into tissue as an electromagnetic field. The electromagnetic treatment device (100) may include a control interface (104), a controller (106), an electromagnetic wave generator (108), and one or more electromagnetic emitters (102) that apply the treatment to the desired portion of the brain or body.

The controller (106) manages the treatment and its parameters by manipulating the electromagnetic wave generator (108) and electromagnetic emitters (102) as per the prescribed treatment. The control interface (104) allows a subject (e.g., patient) or an assistant (e.g., care giver) to start/stop treatments and to view treatment status. The electromagnetic treatment device (100) may be portable so that treatment can be applied while a subject is moving around. Alternatively, the electromagnetic treatment device (100) may be fixed, allowing a subject to receive treatment when positioned correctly relative to the electromagnetic treatment device (100). Electromagnetic emitters (102) may be activated one at a time by the controller (106), or several electromagnetic emitters (102) may be activated to produce electromagnetic (e.g., radio frequency) field combinations to produce controllable patterns where desired on the subject.

As will be described below in more detail, the electromagnetic treatment device (100) provides: 1) immunoregulatory/rebalancing actions to lower or raise brain cytokine levels to provide for reduced risk and less severe diseases of brain aging, and 2) immunoregulatory/rebalancing actions to lower or raise brain and/or body cytokine levels to provide a pathway for increasing life span/longevity. These immunoregulatory/rebalancing actions refer to levels of both pro- and anti-inflammatory cytokines being regulated/rebalanced.

Figure 2:
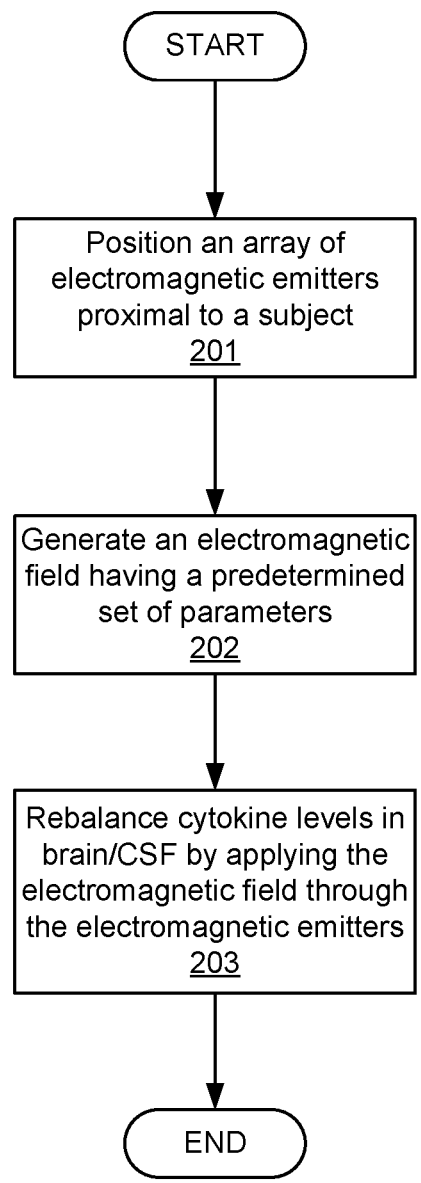
FIG. 2 is a flowchart of a method for normalizing or rebalancing cytokine levels in the brain and/or cerebrospinal fluid (CSF) of a subject, according to an example of the principles described herein.

FIG. 2 is a flowchart of a method (200) for rebalancing/normalizing cytokine levels in the brain/CSF of a subject, according to an example of the principles described herein. According to the method (200), an array of electromagnetic emitters (FIG. 1, 102) are positioned (block 201) proximal to the subject. As described above, such placement may be adjacent to a head surface or adjacent to a body surface of the subject.

The electromagnetic wave generator (FIG. 1, 108) then generates (block 202) electromagnetic waves having a predetermined set of parameters (e.g., electromagnetic wave frequency, power level, pulse repetition rate). In some examples, the waves have a frequency between 1 megahertz (MHz) and 430 GHz (gigahertz), a power level between 0.1 and 16 watts per kilogram (W/kg) average specific absorption rate (SAR), and a pulse repetition rate between 1 and 300 hertz.

The method (200) also includes normalizing/rebalancing (block 203) cytokine levels in an area under the electromagnetic emitters (FIG. 1, 102) by applying electromagnetic waves/fields to the subject through the electromagnetic emitters (FIG. 1, 102). In a particular example, cytokine levels are rebalanced/normalized in the brain, as indexed by cytokine levels in and around the various cellular components of the brain (referred to as brain cells) and/or in the CSF. Some examples of brain cells include microglia, astrocytes, choroid plexus epithelial cells, neurons. In some examples, a treatment session may have a specified duration of, for example, a few minutes to a few hours, or it may be continuous over days, weeks, months, or years. Any given treatment session may be repeated at predetermined intervals, for example, for multiple times a day, week, month, or even years.

There are a number of age-related neurologic diseases/conditions that are characterized by an imbalance of the brain's immune system—specifically, as defined as a dysfunction/imbalance in brain/CSF levels of various cytokines/immune mediators. In most of these diseases and conditions, the immune system's "pro-inflammatory" component is hyperactive, with higher than normal brain/CSF levels of cytokines/immune mediators being present. In this example, normalizing (block 203) cytokine/immune mediator levels involves decreasing pro-inflammatory cytokine levels. Neurologic diseases/conditions wherein such a "pro-inflammatory" environment is present in the brain include Alzheimer's Disease, bacterial or viral brain infections (e.g., COVID-19, Ebola, SARS, certain influenzas), Multiple Sclerosis, Amyotrophic Lateral Sclerosis (ALS), Parkinson's Disease, cognitive impairment in and depression.

A smaller number of age-related neurologic diseases/conditions are characterized by an imbalance of the brain's immune system wherein its pro-inflammatory cytokines are "hypoactive" (i.e., low brain/CSF levels of cytokines). In this example, electromagnetic field application (block 203) involves an increase in brain/CSF cytokine levels. These diseases/conditions include Traumatic Brain Injury (TBI), stroke, AIDS, Mild Cognitive Impairment (MCI), and Alzheimer's Disease (which can involve a hypo- or hyperactive immune system depending on its stage). For both examples, a balancing/rebalancing of anti-inflammatory cytokine levels could also be involved so that both pro- and anti-inflammatory components are in balance.

Regarding Alzheimer's Disease (AD), it may be the case that the disease stage involves uncontrolled brain inflammation (e.g., excess pro-inflammatory cytokines), which may be responsible for at least some of the disease progression from mild to moderate to severe stages. However, the opposite may be the case for the prelude to AD, namely MCI. Here, the brain's immune system is hypoactive (e.g., insufficient pro-inflammatory cytokines), with the resulting inability to resist AD pathogenesis and the ensuing conversion from MCI to AD cognitive impairment. In either case, the present method (200) regulates brain/CSF cytokine levels, which may include reducing brain inflammation in AD or up-regulating cytokine levels in MCI to resist this disease. Such a method (200) also is therapeutic against the neurologic diseases/conditions involving immune system imbalance/dysregulation listed above.

In view of the above, the present specification describes a method (200) for providing electromagnetic field treatment to the brain (e.g., TEMT) or body (e.g., PEMT), which would result in an immunoregulatory effect on brain/CSF by increasing brain/CSF cytokine levels if they are too low or decreasing brain/CSF cytokine levels if they are too high.

These effects would bring both pro- and anti-inflammatory components of the immune system in balance with one another.

As a summary, in a first example of addressing an imbalance in brain/CSF levels of various cytokines, the method (200) includes using an electromagnetic treatment device (FIG. 1, 100) employing an electromagnetic wave generator (FIG. 1, 108), and cable-connected radiating emitters (FIG. 1, 102) on the head to generate and radiate electromagnetic field treatment across the cranium and into the brain of a patient. In some examples, the electromagnetic treatment device (FIG. 1, 100) provides in-home electromagnetic wave treatment while allowing for near complete mobility. Such an electromagnetic treatment device (FIG. 1, 100) may include a custom-printed circuit board (controller (FIG. 1, 106)) powered by a rechargeable battery. The electromagnetic treatment device (FIG. 1, 100), in one example, provides full forebrain TEMT through a constellation of eight specialized electromagnetic emitters (FIG. 1, 102) embedded within a double-layered head cap. In this example, these electromagnetic emitters (FIG. 1, 102) may be activated sequentially, with only one electromagnetic emitter (FIG. 1, 102) active at any given time. When an electromagnetic emitter (FIG. 1, 102) is active, it projects electromagnetic fields into the brain. For this example, computer simulations indicate that electromagnetic fields easily penetrate through the cranium, then the underlying cerebral cortex, and finally into deep sub-cortical brain areas. For treatment purposes, electromagnetic fields are defined as consisting of electromagnetic waves received by an electromagnetic emitter (FIG. 1, 102) that then propagates electromagnetic fields through the air and that then easily penetrate into the brain or body of the patient receiving treatment.

Figure 3A:
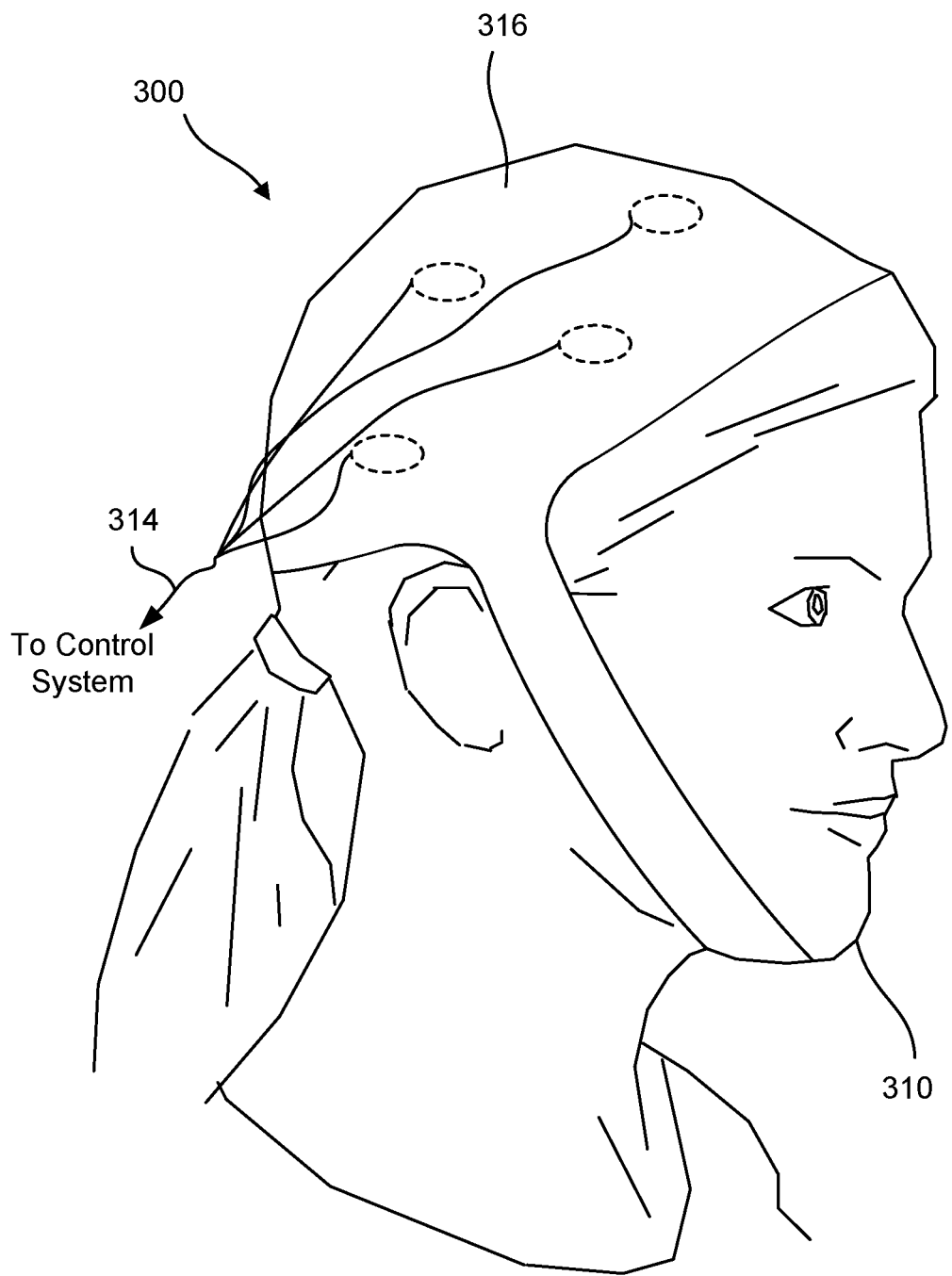
FIGS. 3A-3C depict transcranial electromagnetic treatment (TEMT) to the human head, according to an example of the principles described herein.

FIG. 3A shows a subject (310) wearing a TEMT device (300) called the MemorEM™, which is an example of an electromagnetic treatment device (100) device for providing transcranial electromagnetic treatment (TEMT) to the head discussed in FIG. 1. Electromagnetic waves are generated with a combination control box/battery (not shown) worn on the arm. A cable (314) containing wires connects this control box/battery to each of the electromagnetic emitters (e.g., FIG. 1, 102) located within a double-layered head cap (316). In some examples, the TEMT device (300) may include eight electromagnetic emitters (e.g., FIG. 1, 102) located within a double-layered head cap (316). In some examples, the TEMT device (300) permits near complete mobility in-home, allowing the subject (310) to perform most home activities while receiving electromagnetic treatment. The TEMT device (300) can be adjusted to several power levels, and emits no sound.

Figure 3B:
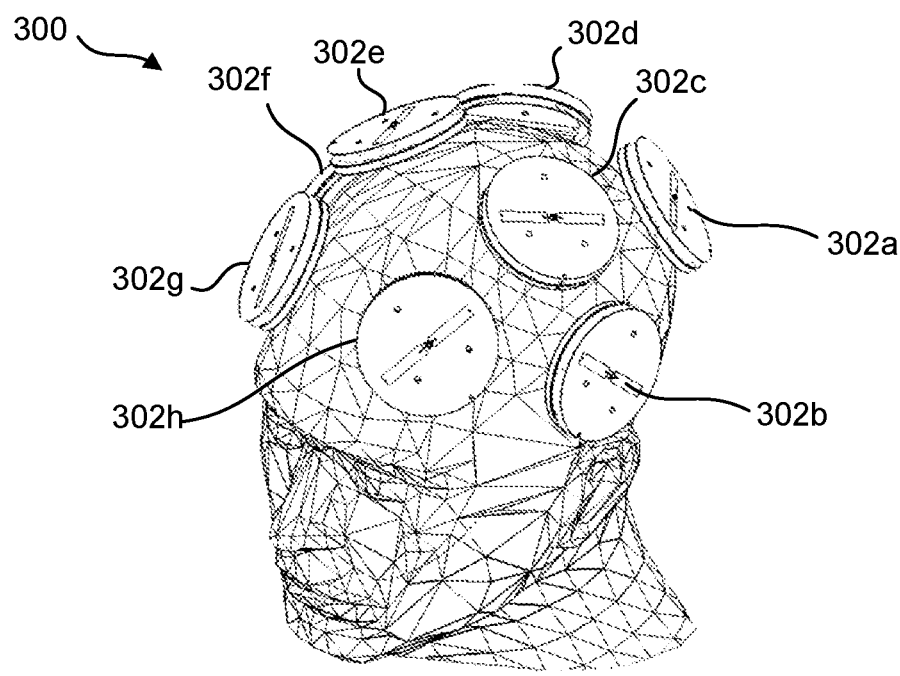

FIG. 3B depicts the size and location of the eight electromagnetic emitters (302a-h) of a TEMT device (300). In some examples, the eight electromagnetic emitters (302a-h) may be enveloped between the two-layer head cap (not shown). Sequential activation of these eight electromagnetic emitters (302a-h) during any given treatment session allows for only one electromagnetic emitter (302) to be active at any given time, although simultaneous activation of several or all emitters can also be accomplished.

Figure 3C:
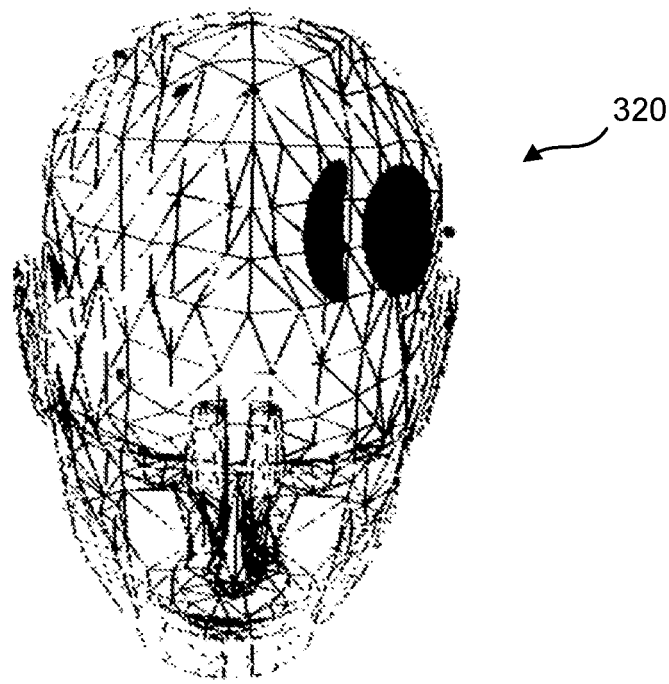

FIG. 3C depicts a finite-difference time-domain (FTDT) computer simulation (320) of the electric field generated by a single active electromagnetic emitter (FIG. 1, 102; FIG. 3B, 302b) set at 915 MHz frequency and 4.0 W/kg Specific Absorption Rate (SAR). Given the distribution and penetration depth of the electric field from this one active electromagnetic emitter (102) into the brain's temporal lobe, it can be appreciated that all electromagnetic emitters (302a-h) during any given treatment provide for full forebrain electromagnetic field treatment. In some examples, there may be around 200 treatment cycles (emitter activations) per second, but this "pulse repetition rate" may be lower (e.g., 40 Hz) or higher (e.g., 250 Hz).

The electromagnetic device described above (FIG. 1, 100; FIG. 3A, 300; and FIG. 3B, 300) provides electromagnetic treatment not only to neurons and glial cells that make up the cellular part of the brain, but also to cerebral vessels on the surface of the brain and deep cerebral vessels located within or below the cerebral cortex. That is, the area under the electromagnetic emitters (FIG. 1, 102; FIG. 3B, 302a-h) includes the brain's functional cells and cerebral vessels going through or on top of the brain. As such, the cellular components of blood circulating through those cerebral vessels (e.g., lymphocytes) or the vessels themselves could be affected by electromagnetic fields emanating from electromagnetic emitters (FIG. 1, 102; FIG. 3B, 302a-h) positioned on the head's surface.

Figure 4:
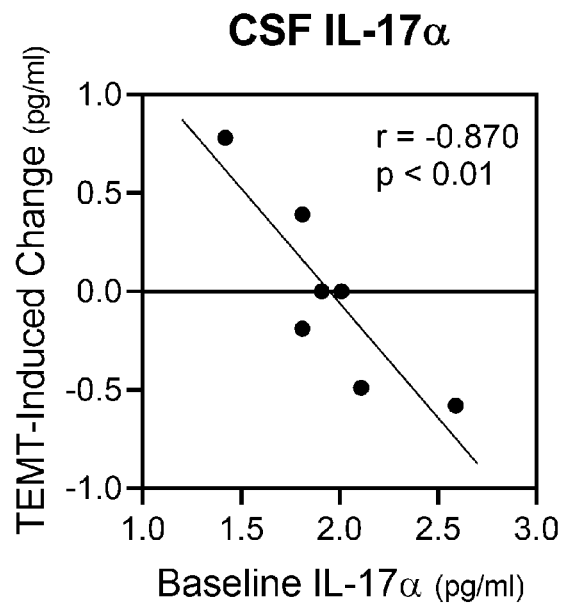
FIG. 4 is a graph showing the immunoregulatory/rebalancing ability of TEMT in the Alzheimer's disease (AD) brain/CSF by displaying a strong correlation between baseline levels of the cytokine IL-17α in CSF of individual AD subjects and both the direction and extent of TEMT-induced change in IL-17α after 2 months of daily treatment.
Figure 5:
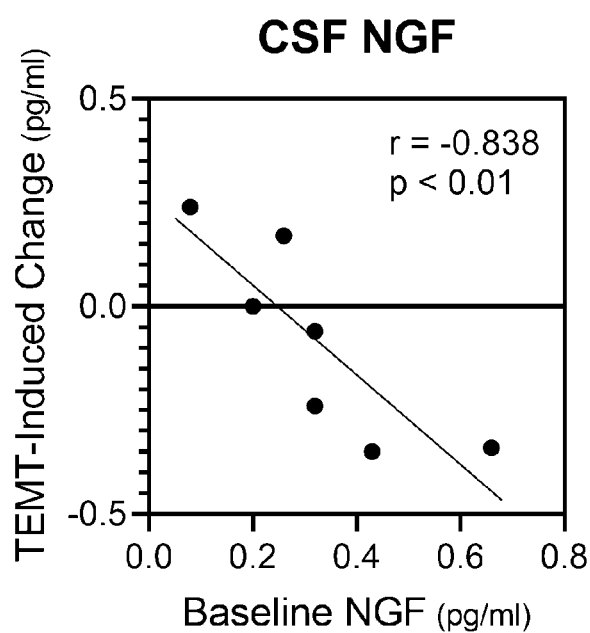
FIG. 5 is a graph showing the immunoregulatory/rebalancing ability of TEMT in the Alzheimer's brain/CSF by displaying a strong correlation between baseline levels of the cytokine nerve growth factor (NGF) in CSF of individual AD subjects and both the direction and extent of TEMT-induced change in NGF after 2 months of daily treatment.
Figure 6:
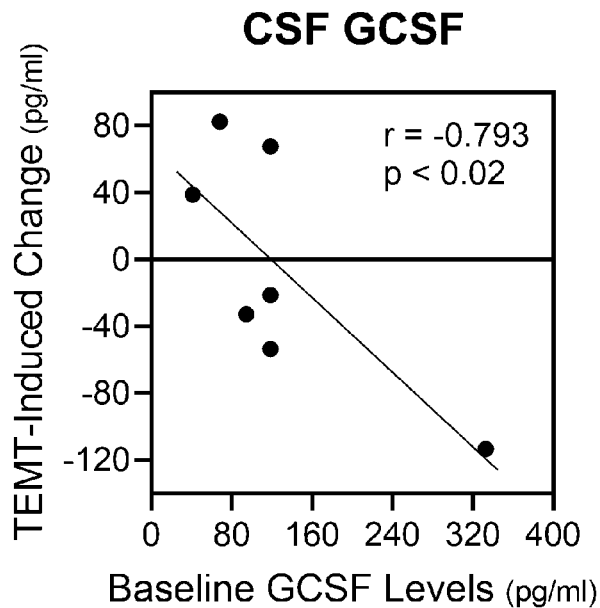
FIG. 6 is a graph showing the immunoregulatory/rebalancing ability of TEMT in the Alzheimer's brain/CSF by displaying a strong correlation between baseline levels of the cytokine granulocyte colony-stimulating factor (GCSF) in CSF of individual AD subjects and both the direction and extent of TEMT-induced change in GCSF after 2 months of daily treatment.

In clinical studies that administered TEMT through MemorEM™ devices to mild and moderate AD subjects, cerebrospinal fluid (CSF) samples were taken at baseline and after 2 months of twice-daily, 1-hour treatments. CSF is a well-established index of brain constituency and functional activity; CSF is known as a non-invasive window into the brain. Analysis of CSF for five cytokines/immune mediators (IL-17α, NGF, GCSF, VEGF, and TGFα) measurable in the CSF revealed a clear immunoregulatory/rebalancing ability of TEMT, irrespective of whether they were primarily pro- or anti-inflammatory cytokines. Specifically, if baseline cytokine levels were low (below normal), 2 months of TEMT resulted in elevated cytokine levels. Conversely, if CSF cytokine levels were high, TEMT induced a reduction in their levels. Highly significant correlations were present for all five of these CSF cytokines, as exemplified for IL-17α (illustrated in FIG. 4), NGF (illustrated in FIG. 5), and GCSF (illustrated in FIG. 6). Correlation coefficient values/significance for the other two cytokines (VEGF and TGFα) were [r=−0.806; p<0.05] and [r=−0.716; p<0.05], respectively. These five significant correlations indicate that baseline levels of CSF cytokines/immune mediators determine the direction and extent of their response to TEMT. This is clearly an immunoregulatory/rebalancing action of TEMT in the brain.

Figure 7:
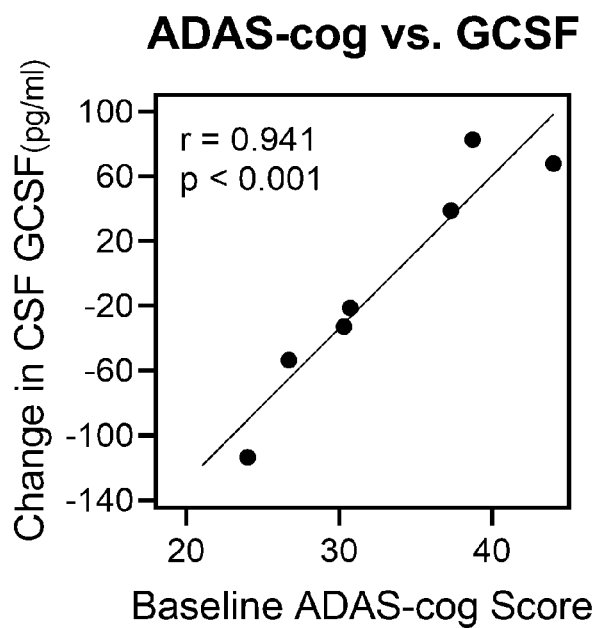
FIG. 7 is a graph showing that the direction and change in brain/CSF levels of the cytokine GCSF induced by TEMT is strongly associated with the degree of cognitive impairment (e.g., as indexed by the Alzheimer's Disease Assessment Scale-Cognitive Subscale (ADAS-Cog) test) in individual AD subjects.

The ADAS-cog score of AD subjects is the clinical benchmark for determining their disease stage and any effects of therapeutic interventions. For the cytokine GCSF in CSF, baseline ADAS-cog score correlated strongly with the direction and extent of the GCSF response to TEMT [r=0.941; p, <0.001] (illustrated in FIG. 7). Higher (poorer) ADAS-cog scores at baseline resulted in increased GCSF levels in CSF, while just the opposite occurred for lower (better) ADAS-cog scores. This correlation demonstrates that the level of cognitive impairment is strongly associated with the direction and changes in brain/CSF cytokines induced by TEMT. Such TEMT effects to increase GCSF levels in CSF of AD subjects with poorer cognitive performance are not inconsequential in view of the multiple beneficial effects that GCSF has on brain synaptogenesis, microglial activity, and neurogenesis.

CSF levels of GCSF (and TGFα) were much higher than their plasma levels in all AD subjects. Therefore, it is clear that cells in the AD brain are secreting GCSF and that their secretion of GCSF is affected by TEMT administration. It is known that AD transgenic mice given three weeks of GCSF injections showed central nervous system (CNS) enhancements in hippocampal neurogenesis, microglial activation/Aβ degradation, and synaptogenesis. These three beneficial effects would be anticipated to be enhanced by TEMT in those AD subjects who had low baseline GCSF levels in CSF, all of whom showed TEMT-induced increases in CSF levels of GCSF.

The exact mechanism(s) of TEMT effects on brain cytokine levels in AD subjects is currently unknown. Microglia, as well as astrocytes, both secrete cytokines. Thus, TEMT may affect cytokine secretion from one or both of these CNS cell types. Stimulated/activated microglia and astrocytes undergo a pro-inflammatory response by releasing inflammatory cytokines. In this regard, electromagnetic wave effects may be observed in both microglia and astrocytes. Specifically, brain microglial activation may be histologically-observed in rats following their exposure to 915 MHz radiofrequency waves. Similarly, microglia in cell culture given a single 20 minute electromagnetic field (EMF) exposure at 2450 MHz were activated, resulting in a pro-inflammatory secretion of TNFα. By contrast, 1500 MHz radiofrequency waves can inhibit proliferation of microglia in the brain. Astrocytes in cell culture may be activated by exposure to 900 MHz electromagnetic waves. These EMF exposure studies in cell cultures or rodents indicate the ability of 900 MHz EMF (or the 915 MHz used in the clinical studies of this description) to affect both brain microglia and astrocytes. An alternative mechanism of CNS/CSF cytokine regulation by TEMT may be through affecting choroid plexus epithelium cells, which also secrete cytokines into the CSF (which the choroid plexus epithelium cells produce). As well, the release of cytokines by neurons is known to occur. Therefore, combinations of the aforementioned four brain cell types (microglial, astrocytes, choroid plexus epithelial cells, and/or neurons) may respond to TEMT by "rebalancing" multiple pro- and anti-inflammatory cytokines in the brain/CSF.

Figure 8:
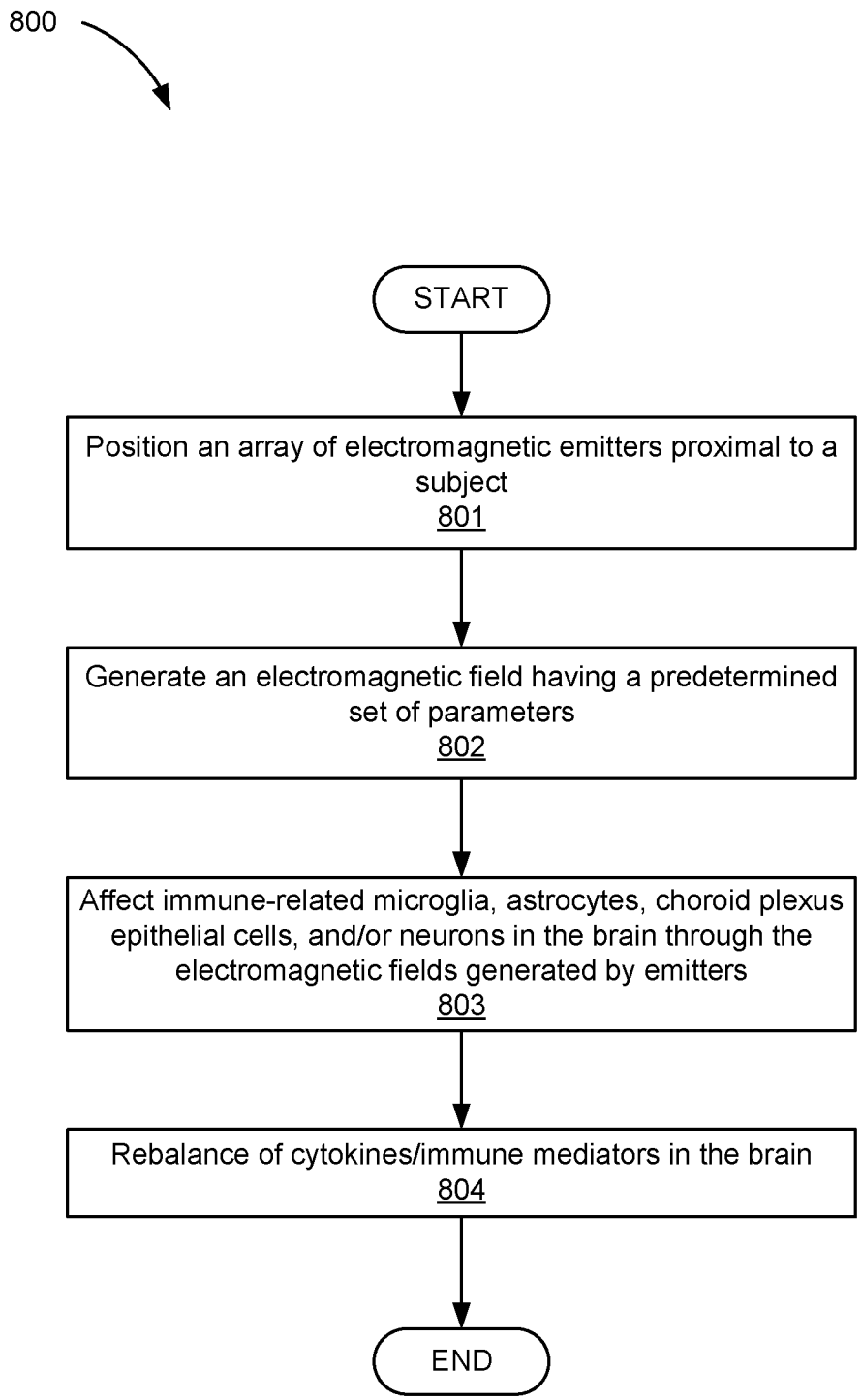
FIG. 8 is a flowchart of a method for rebalancing cytokine/immune mediator levels in the brain/CSF of a subject by affecting various immune-related cell types in the brain, according to another example of the principles described herein.

FIG. 8 is a flowchart of a method (800) for rebalancing or immunoregulating cytokine levels in the brain of a subject, according to an example of the principles described herein. The method (800) may include positioning (block 801) an array of electromagnetic emitters (FIG. 1, 102) proximal to a subject, generating (block 802) electromagnetic waves/fields having a predetermined set of parameters (e.g., electromagnetic wave frequency, power level, pulse repetition rate), affecting one or more of the brain's immune-related microglia, astrocytes, choroid plexus epithelial cells, and neurons with such electromagnetic waves (block 803) to rebalance cytokine levels in the brain/CSF (804).

Figure 9:
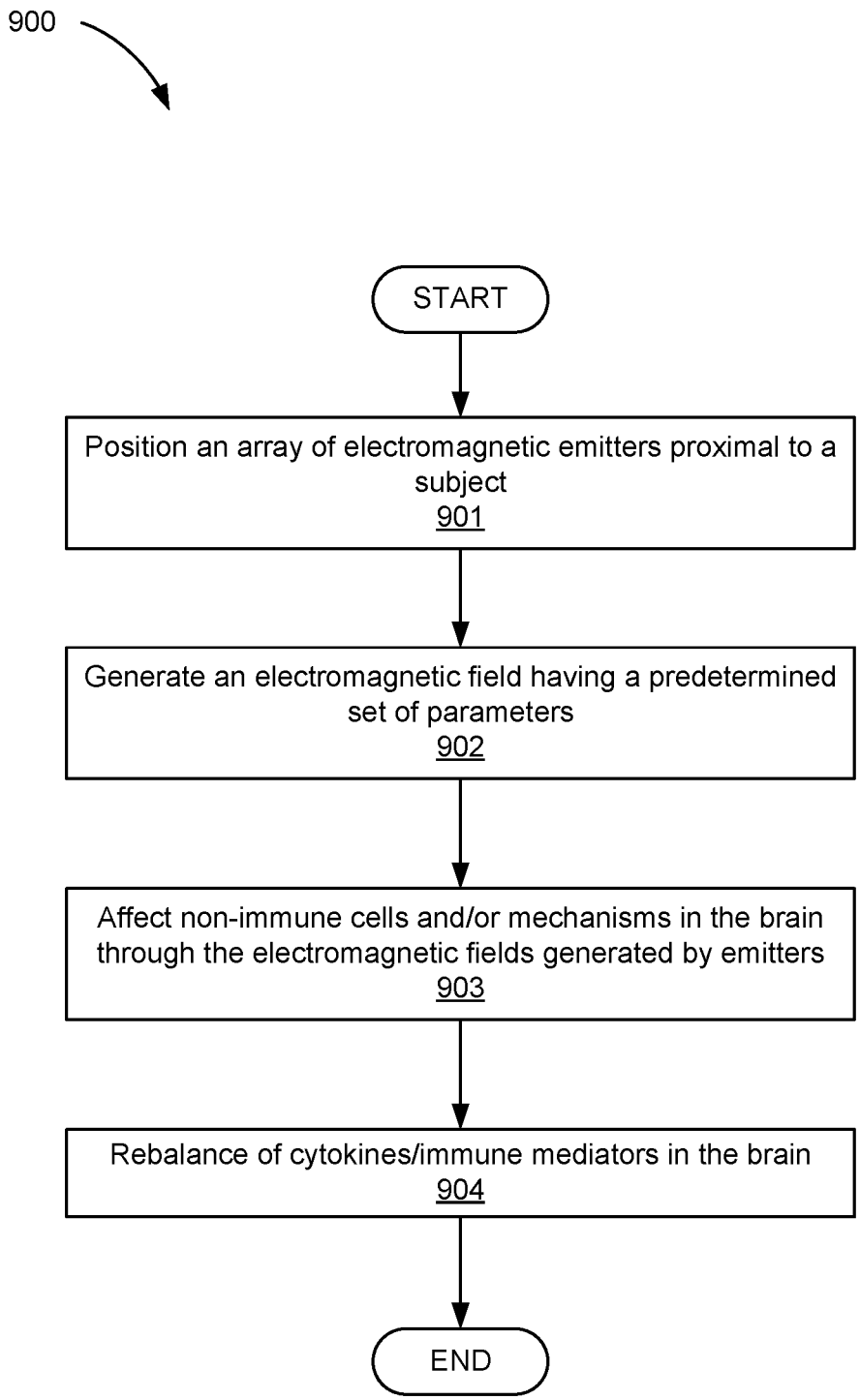
FIG. 9 is a flowchart of a method for rebalancing cytokine/immune mediator levels in the brain/CSF of a subject by affecting non-immune cells and/or mechanisms in the brain, according to another example of the principles described herein.

FIG. 9 is a flowchart of a method (900) for rebalancing or immunoregulating cytokine levels in the brain of a subject, according to another example of the principles described herein. Alternatively or in concert with the flow chart in FIG. 8, TEMT may act through "non-immune" cells or mechanisms to rebalance cytokine levels in the brain/CSF according to the example of FIG. 9. The method (900) may include positioning (block 901) an array of electromagnetic emitters (FIG. 1, 102) proximal to a subject, generating (block 902) electromagnetic waves/fields having a predetermined set of parameters (e.g., electromagnetic wave frequency, power level, pulse repetition rate), affecting (block 903) one or more non-immune cells or mechanisms in the brain with such electromagnetic waves to rebalance (block 904) cytokine levels in the brain/CSF.

The methods and results described herein have widespread implications since brain diseases/conditions characterized by a hypo-active brain immune system could have the "pro-inflammatory" component of this immune system re-activated (rebalanced) by TEMT. For example, in the case of mild cognitive impairment (MCI) or very early AD, the reactivated and rebalanced brain immune system could prevent or resist AD pathogenesis. A similar, but opposite scenario, can be envisioned for brain diseases/conditions characterized by a hyper-active brain immune system (i.e., one with a dominant "pro-inflammatory" component).

It is assumed that such profound immunoregulatory ability of TEMT would also be evident in "normal" individuals without diseases/conditions involving immune dysfunction, wherein abnormally low or high cytokine levels in CSF may nonetheless be present and can be corrected by TEMT (or PEMT). Such a situation may be envisioned as subjects age from having immune balance in middle age to immune imbalance thereafter. Thus, TEMT (or PEMT) may maintain the immune balance characteristic of middle age in humans.

It should be noted that among the brain/CSF cytokines exhibiting immunoregulation by TEMT, this regulation was predictably in a given direction. For example, the AD subjects who had higher than normal brain levels of these cytokines typically responded to TEMT with a reduction in levels for all cytokines that were high—and vice versa for subjects who had cytokines that are below normal levels. Thus, the described methods provide a comprehensive immunoregulation/rebalancing of brain cytokines toward a convergence level irrespective of whether a given cytokine is pro- or anti-inflammatory. This is a unique and widespread immunoregulatory ability of TEMT (or PEMT) not exhibited by any other known technology or drug.

In yet another example of addressing imbalance in brain levels of various cytokines/immune mediators, the methods described herein may be performed on a "body" of a user using a peripheral electromagnetic treatment (PEMT) device employing an electromagnetic wave generator (FIG. 1, 108), and cable-connected electromagnetic emitters (FIG. 1, 102) to generate and radiate electromagnetic field treatment into the body of the subject beneath the electromagnetic emitter(s) (FIG. 1, 102). In one specific example, there may be one or multiple electromagnetic emitters (FIG. 1, 102) depending on the brain disease/condition to be treated. As an example, a subject with serious COVID-19 infection involving the brain may require multiple electromagnetic emitters (FIG. 1, 102) positioned bilaterally on the neck, axial arm region, and lower chest in order to suppress the brain inflammation, systemic cytokine storm, and lower lung inflammation typical of serious COVID-19 infections.

Figure 10:
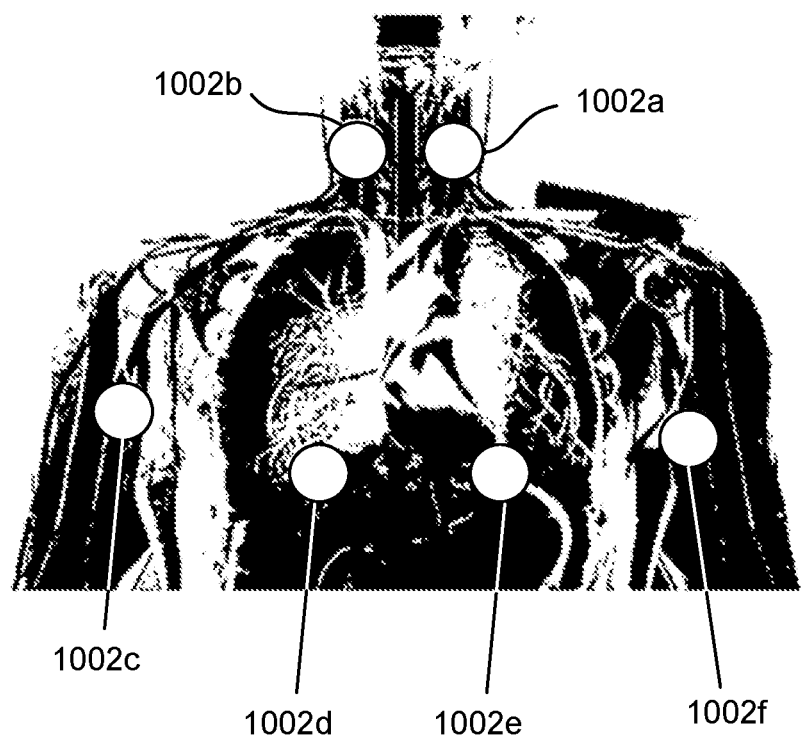
FIG. 10 depicts body/peripheral electromagnetic treatment (PEMT), specifically with electromagnetic emitters located above major arterial, venous, and lymphatic vessels in the neck and axial region of the arm, as well as above the lower lung.

FIG. 10 illustrates an example of PEMT for addressing imbalance in brain levels of various cytokines/immune mediators via EMF applied to the body of a subject. In this example, peripheral PEMT emitters 1002a-f may be used to indirectly affect brain inflammation through systemic vascular or lymphatic mechanisms or some other indirect mechanism. In any event, the effect would be to lower the high brain cytokine levels (inflammation) of the COVID-19 patient. Although it is apparent that direct TEMT treatment of brain inflammation in this example would probably provide the best results, the possibility of beneficial systemic mechanisms by PEMT on brain inflammation should not be dismissed.

The presently described "rebalancing" effects of TEMT or PEMT in AD subjects may have far-reaching therapeutic benefits for other neurologic disorders characterized by immune system imbalance, such as Parkinson's Disease, Lewy Body dementia, Frontotemporal lobe dementia, LATE dementia, ALS, and stroke—all of which are characterized by an imbalance of pro- vs. anti-inflammatory cytokines in either their brain/CSF or vasculature.

In all the above examples and many more applications of either TEMT or PEMT to meet addressing imbalance in brain/CSF levels of various cytokines/immune mediators, the following ranges of electromagnetic wave parameters being emitted may be used:
  a. an electromagnetic wave frequency of 1 MHz to 430 GHz
  b. a power level of 0.1 to 16 W/kg average Specific Absorption Rate (SAR)
  c. a pulse repetition rate of 1 to 300 Hz
  d. a duty cycle between 1% and 100% (continuous).

Accordingly, the present specification describes a method of applying electromagnetic fields to alter brain cytokine/immune mediator levels in a subject by: 1) directly activating or suppressing cytokine/immune mediator release from brain cells having an immunologic function (e.g., microglia, astrocytes, choroid plexus epithelial cells, and neurons) through TEMT, and 2) by indirectly affecting brain cells having an immunologic function through PEMT.

Figure 11:
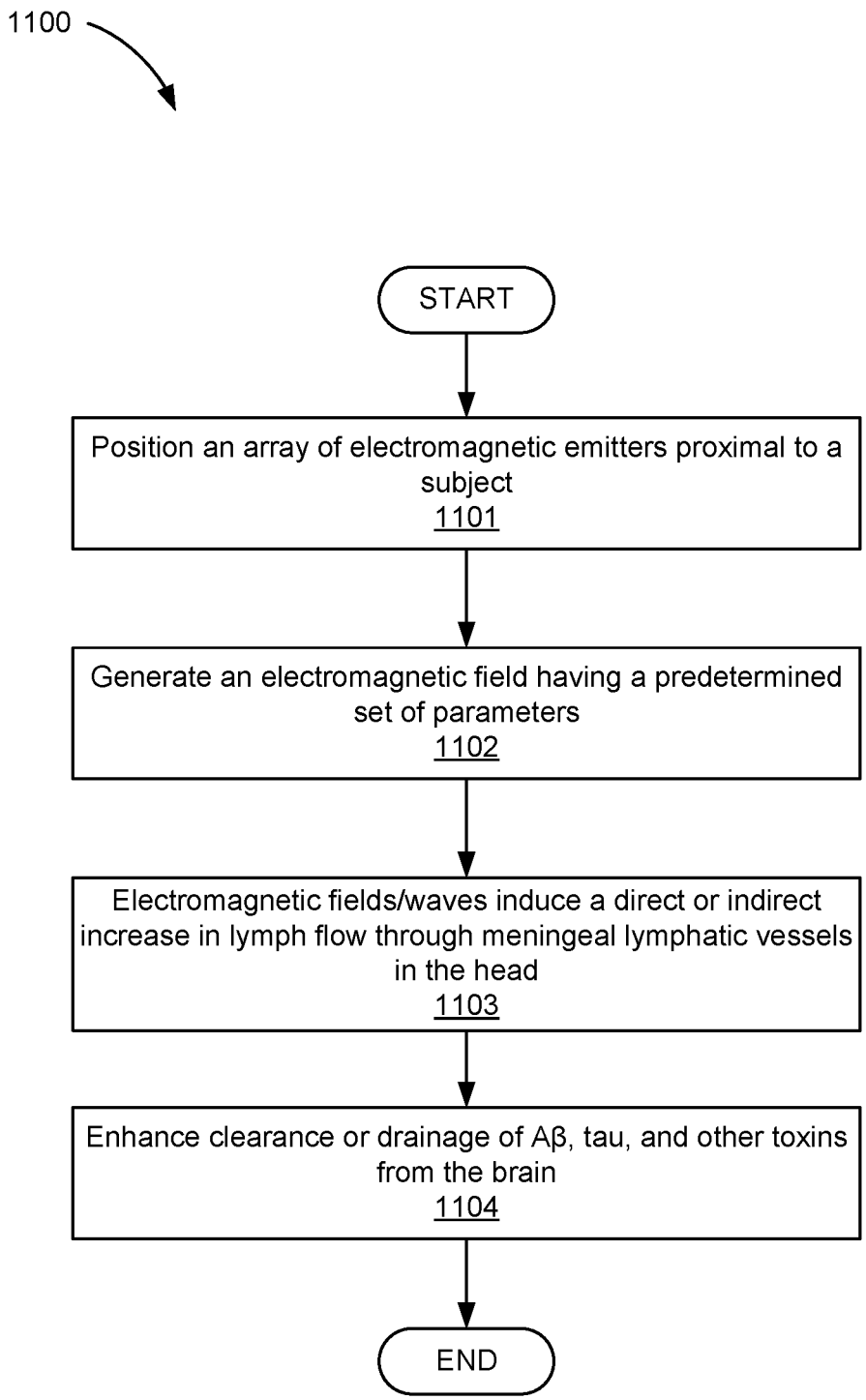
FIG. 11 is a flowchart of a method for increased lymph flow through meningeal lymphatic vessels in the brain to enhance clearance/removal of toxins from the brain, according to an example of the principles described herein.

FIG. 11 is a flowchart of a method (1100) for increased lymph flow through meningeal lymphatic vessels in the brain to enhance clearance/removal of toxins from the brain, according to an example of the principles described herein. In this example, the method (1100) may be utilized for removal of toxic proteins from the brain. Until recently, it was assumed that the only route to clear toxins such as soluble β-amyloid (Aβ) and tau from the brain was via their transport through the cerebrospinal fluid (CSF) and then into the venous blood. However, it has since been determined that the brain has an extensive system of "meningeal" lymphatic vessels that are primarily in two brain locations: 1) on the dorsal aspect of the brain, parallel to dural venous sinuses and the middle meningeal arteries, and 2) at the base of the brain relative to the skull. The brain's interstitial fluid surrounding its neurons and glial cells is drained unidirectionally into CSF, then into these meningeal lymphatic vessels as lymph, which is then transported down the neck and into cervical lymph nodes. These lymph nodes then drain the lymph into large veins to clear various toxins from the brain. As such, these meningeal lymphatic vessels and their one-way lymph flow to the venous system represents a second route (in addition to the CSF) for toxic protein clearance from the brain.

The meningeal lymphatics have become a target for AD therapeutics since an increase in their lymph flow would remove more toxic Aβ and tau soluble aggregates (currently considered to be the root causes of AD) from the brain. Greater lymph flow in these vessels may enhance clearance of such brain toxins. Therefore, a methodology that increases flow in those lymphatic vessels (e.g., by vessel dilation) may enhance Aβ and tau clearance from the brain, along with other toxins. A facilitated removal of Aβ and tau from the brain would be highly desirable in view of TEMT's primary action in the brain being to disaggregate soluble oligomers and insoluble deposits of these brain toxins, thus necessitating their enhanced clearance from the brain.

Specifically, the method (1100) may involve positioning (block 1101) electromagnetic emitters proximal to the subject's brain (TEMT) or body (PEMT) to generate (block 1102) electromagnetic waves having a predetermined set of parameters (e.g., electromagnetic wave frequency, power level, pulse repetition rate). The resulting electromagnetic fields/waves directly or indirect induce increased flow (block 1103) through meningeal lymphatic vessels in the head to increase clearance or drainage of β-amyloid (Aβ) and tau isoforms, along with other brain toxins and metabolites, from the brain (1104). The enhanced removal of Aβ and tau from the brain via a TEMT-induced increase in meningeal lymphatic flow could be extraordinarily important to stop or reverse AD cognitive impairment. Indeed, a dysfunction in clearance of these two toxic proteins has been hypothesized to be a major reason for why their oligomeric and insoluble forms build up in the AD brain.

In view of the above, drainage (block 1104) of Aβ and tau isoforms, along with other brain toxins and metabolites, can be done by applying electromagnetic fields, through TEMT to the human head or possibly through PEMT to the human body, by electromagnetic emitters (FIG. 1, 102) positioned on either the head or body surface, respectively. Doing so directly or indirectly increases removal of toxins (e.g., Aβ, tau) from the brain via enhanced meningeal lymphatic flow/drainage.

In the above example and other applications of either TEMT or PEMT to clear Aβ and tau isoforms, along with other brain toxins and metabolites, the following ranges of electromagnetic wave parameters being emitted are possible:
  a. an electromagnetic wave frequency of 1 MHz to 430 GHz
  b. a power level of 0.1 to 16 W/kg average Specific Absorption Rate (SAR)
  c. a pulse repetition rate of 1 to 300 Hz
  d. a duty cycle between 1% and 100% (continuous)

Throughout evolution, humans have been set to live approximately 40-50 years. However, with current life expectancy being into the late 70s or 80s, the immune system has to be active longer than in past centuries. This prolonged period of activation leads to chronic inflammation, such that humans in developed countries spend only around 75-80% of their lifespan in good health. Aging, itself, is characterized by a state of reduced ability to maintain health. A loss of homeostasis (imbalance) in cytokine networks with aging contributes substantially to this health loss in old age.

For almost two decades now, negative health effects of electromagnetic waves (particularly within the radiofrequency range) have been forwarded by the media and by some in the scientific community, with little supportive real-world evidence. These purported negative health effects have largely involved animals exposed to very high EMF power levels or uncontrolled human epidemiologic (retrospective) studies within a small geographical area of Europe. In any event, such purported negative health effects of electromagnetic fields (particularly radiofrequency fields emitted by cell phones) include an increased occurrence and severity of age-related diseases, which consequently would be expected to shorten human life span.

However, the systems and methods described in this specification, supported by concurrently-presented human data, demonstrate that TEMT can regulate and rebalance cytokine levels in the human body—both pro-inflammatory and anti-inflammatory cytokines. Such cytokine rebalancing benefits by the presently-described systems and methods are in alignment with studies showing that centenarians (100+ years of age) have a robust and "balanced" immune system of both pro-inflammatory and anti-inflammatory components in their bodies. This is in sharp contrast to the "unbalanced" immune system typical of humans after middle-age, wherein the pro-inflammatory component becomes dominate, resulting in a state of "inflamm-aging" and the multitude of ensuing diseases/disorders that thus limit human life span. It would be anticipated that any intervention, process or system that provides or restores a "balanced" and robust immune system of pro- and anti-inflammatory components during human aging would mimic the "balanced", vigorous immune system characteristic of most centenarian and thus result in the same increase in healthy longevity (e.g., increased "health span") that centenarians enjoy.

Figure 12:
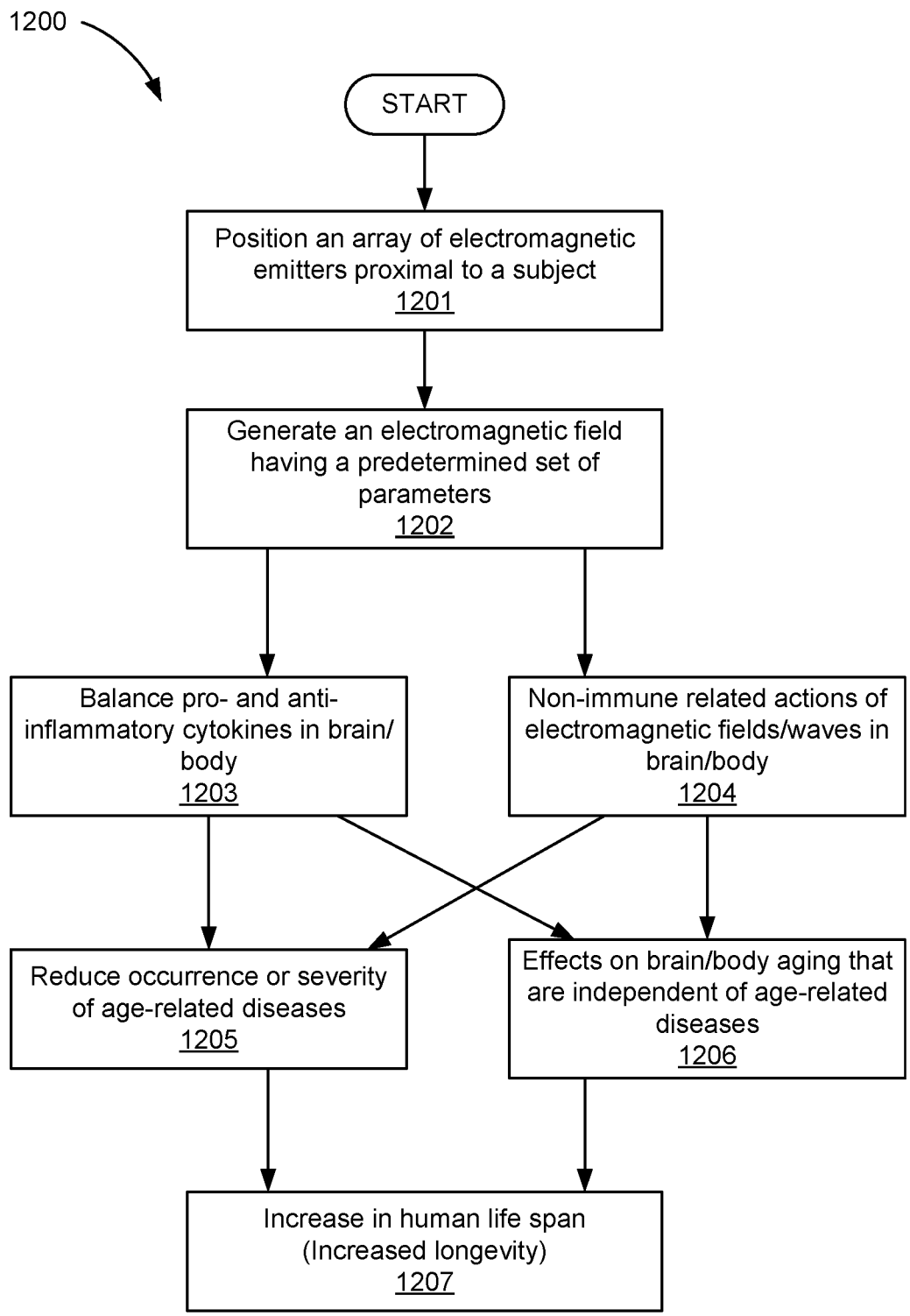
FIG. 12 is a flowchart of a method for increasing human life span (longevity) by reducing age-related diseases and/or through mechanisms independent of age-related diseases, according to an example of the principles described herein.

FIG. 12 is a flowchart of a method (1200) for increasing human life span (longevity) via electromagnetic treatment, according to an example of the principles described herein. As described above, the method (1200) includes positioning (block 1201) an array of electromagnetic emitters proximal to a subject's head (TEMT) or body (PEMT) and generating (block 1202) electromagnetic fields/waves having a predetermined predetermined set of parameters (e.g., electromagnetic wave frequency, power level, pulse repetition rate). According to this method (1200), such electromagnetic treatment may be employed at any time during human aging and for as long as desired to increase life span. The electromagnetic treatment-induced increase (block 1207) in human life span could result from any number of actions/mechanisms provided by this treatment. One such mechanism is the ability of treatment to balance or rebalance (block 1203) both brain and body pro- and anti-inflammatory cytokines, although other "non-immune related" actions/mechanisms of treatment (block 1204) may be involved separately or in combination. According to this method (1200), such actions/mechanisms of treatment result in increased life span through a reduced risk or severity of age-related diseases (block 1205) and/or through effects that are independent of age-related diseases (block 1206), such as effects on genetic background/markers, mitochondrial energy production, or antioxidant defenses.

It is important to recognize that the genetic component to longevity is only around 25%, suggesting that the presently described rebalancing of the immune system by TEMT and/or PEMT could have dramatic life-extending effects through the remaining 75% of longevity factors. Regarding the genetic component to longevity, at least two "longevity" loci have been identified as being associated with human survival beyond 90 years of age: 1) rs2149954 on chromosome 5q33.3, and 2) rs4420638 on chromosome 19z13.32.

Centenarians seem to be equipped with gene variants that allow them to have a balanced immune system with both pro- and anti-inflammatory components being robust. Along this line, centenarians have a higher frequency of genetic markers associated with better control of inflammation, so their immune system's pro-inflammatory component does not over-react to potentially damaging agents and is countered by a strong anti-inflammatory component.

Thus, healthy aging and longevity are not the result of only a lower propensity to mount pro-inflammatory responses, but also of an efficient and equally prominent anti-inflammatory network. If an "inflamm-aging" profile is the key to our understanding human aging, attaining a strong anti-inflammaging profile could be the key to longevity in good health (a longer "health span"). TEMT and/or PEMT can provide for a strong anti-inflammaging profile by increases body levels of anti-inflammatory cytokines when they are too low.

The benefits of the described systems and methods in this specification for healthy aging, and their strong interconnection with a balanced immune system as key to longevity, lead to conclusions and claims that are opposite of common believe and some scientific literature purporting a negative effect of electromagnetic/radiofrequency waves on human longevity. Rather, the present description asserts that electromagnetic/radiofrequency waves, as would be administered by a TEMT/MemorEM™ device or PEMT, actually increase human life span and in good health (i.e, provide an increase in health span). This human life extension could occur through an EMF-induced decrease in occurrence or severity of age-related diseases and/or through some alternative and independent EMF-induced mechanism(s) or effects, as previously indicated.

Age-related diseases/conditions that TEMT and/or PEMT could reduce the occurrence and/or severity of through immune system rebalancing (FIG. 12, block 1205) and/or through effects that are independent of immune system rebalancing (FIG. 12, block 1206) include the following: all forms of dementia, all forms of cardiovascular disease, all forms of cancer of the body, AIDS, traumatic brain injury, chronic traumatic encephalopathy, post-operative cognitive dysfunction, cognitive impairment after anesthesia, Rheumatoid Arthritis, bacterial or viral infections (e.g., COVID-19, Ebola, SARS), Rheumatoid Arthritis, Multiple Sclerosis, arterial hypertension, autoimmune diseases, all forms of depression and anxiety, cognitive impairment in depression, allergy, asthma, coeliac disease, glomerulonephritis, hepatitis, inflammatory bowel disease, osteoarthritis, atherosclerosis, diabetes, COPD, chronic kidney disease, and metabolic syndrome.

In the above example and other applications of TEMT or PEMT to increase life span through reduced aged-related disease occurrence/severity and/or independent of age-related disease reduction, the following ranges of electromagnetic wave parameters being emitted are possible:

a. an electromagnetic wave frequency of 1 MHz to 430 GHz
b. a power level of 0.1 to 16 W/kg average Specific Absorption Rate (SAR)
c. a pulse repetition rate of 1 to 300 Hz
d. a duty cycle between 1% and 100% (continuous)

Figure 13A:
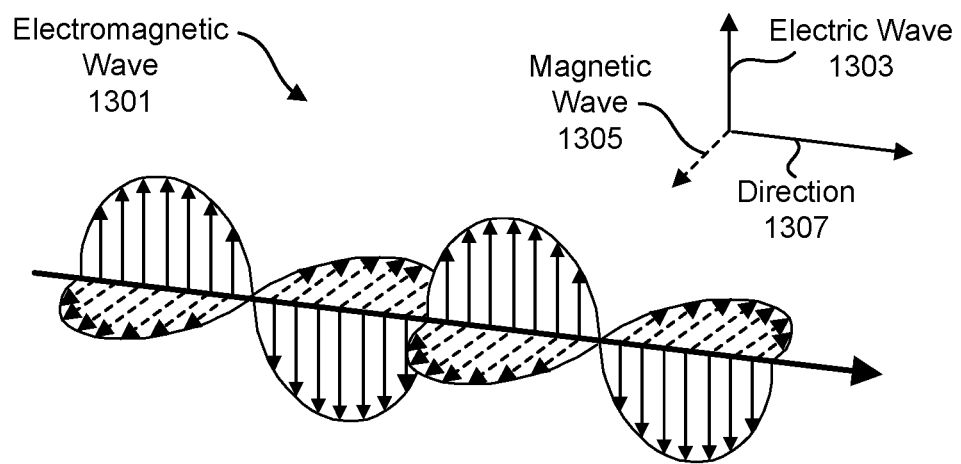
FIGS. 13A-13B illustrate differences between TEMT electromagnetic waves having interdigitated electric and magnetic waves and magnetic waves generated by magnets.

As used in the present specification and in the appended claims, the term "electromagnetic fields" or "electromagnetic treatment" refer to interdigitated electric and magnetic waves generated by an electromagnetic wave generator, sent to an emitter and then passed into tissue as electromagnetic fields/treatment. FIG. 13A illustrates an example of TEMT electromagnetic waves (1301) having interdigitated electric waves (1303) and magnetic waves (1305) moving in a given direction (1307).

Figure 13B:
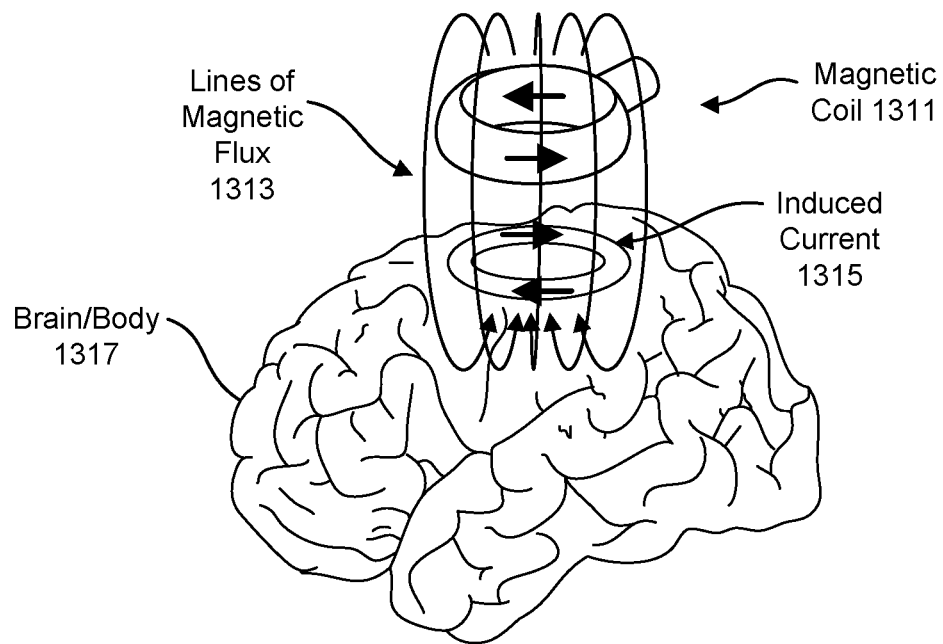

FIG. 13B illustrates an example of magnetic waves generated by magnets. In this example, a magnetic coil (1311) generates a magnetic flux (1313), which induces a current (1315) in the brain/body (1317). It should be noted that the present specification is not referring to "magnetic stimulation/treatment", which involves generation of magnetic waves (e.g., magnetic flux (1313)) into a tissue by magnets, with ensuing induction of completely separate electric waves at a right angle to the magnetic waves in the tissue. Such magnetic stimulation is often, but erroneously, referred to as "electromagnetic stimulation, electromagnetic waves, or Pulsed Electromagnetic Fields (PEMF's)". Thus, magnetic stimulation is a completely different neuromodulatory technology from TEMT that does not provide true electromagnetic treatment. This is amply demonstrated by looking at the units of power: electromagnetic waves of TEMT and PEMT use Watts/kg or Specific Absorption Rate (SAR), while magnetic waves use "tesla" magnetic units.

The preceding description has been presented only to illustrate and describe the invention. It is not intended to be exhaustive or to limit the invention to any precise form disclosed. Many modifications and variations are possible in light of the above teaching.

The examples described herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. A method of normalizing or rebalancing immune mediator levels in a brain of a subject, the method comprising:
positioning proximal to the subject an array of one or more electromagnetic emitters of a transcranial electromagnetic treatment (TEMT) device or of a peripheral electromagnetic treatment (PEMT) device;
generating, by an electromagnetic wave generator, an electromagnetic field having a predetermined set of parameters including a frequency of 1 megahertz (MHz) to 430 gigahertz (GHz), an average Specific Absorption Rate (SAR) of 0.1 to 16 watts per kilogram (W/kg), a pulse repetition rate of 1 to 300 hertz (Hz), or a duty cycle between 1% and 100%; and
applying the electromagnetic field to the subject through the at least one electromagnetic emitter in the array to rebalance the brain-immune mediator levels in an area under at least one electromagnetic emitter in the array of one or more electromagnetic emitters.

2. The method of claim 1, wherein applying the electromagnetic field to the subject through the at least one electromagnetic emitter in the array includes normalizing or re-balancing immune mediator levels in brain interstitial fluid, cerebrospinal fluid (CSF), or vascular fluid beneath the at least one electromagnetic emitter.

3. The method of claim 1, wherein the array of the one or more electromagnetic emitters includes at least one electromagnetic emitter of the TEMT device that is positioned adjacent a head surface of the subject.

4. The method of claim 1, wherein the array of the one or more electromagnetic emitters includes at least one electromagnetic emitter of the PEMT device that is positioned adjacent a body surface of the subject.

5. The method of claim 1, wherein the area under the at least one electromagnetic emitter includes glial of the brain, choroid plexus epithelial cells, or neurons of the brain.

6. The method of claim 1, wherein applying the electromagnetic field to the subject through the at least one electromagnetic emitter in the array includes activation or suppression of the immune mediator release from brain cells.

7. The method of claim 1, wherein applying the electromagnetic field to the subject through the at least one electromagnetic emitter in the array includes increasing the brain immune mediator levels when initial brain immune mediator levels are low.

8. The method of claim 7, wherein applying the electromagnetic field to the subject through the at least one electromagnetic emitter in the array includes increasing the brain immune mediator levels for the subject with at least one of Traumatic Brain Injury (TBI), stroke, acquired immunodeficiency syndrome (AIDS), Mild Cognitive Impairment (MCI), or Alzheimer's Disease.

9. The method of claim 1, wherein applying the electromagnetic field to the subject through the at least one electromagnetic emitter in the array includes decreasing the brain immune mediator levels when initial brain immune mediator levels are high.

10. The method of claim 9, wherein applying the electromagnetic field to the subject through the at least one electromagnetic emitter in the array includes decreasing the brain immune mediator levels for the subject with at least one of Alzheimer's Disease, Frontotemporal Lobe dementia, Lewy Body Dementia, Limbic-Predominant Age-Related TPD-43 Encephalopathy (LATE) dementia, Vascular dementia, brain bacterial or viral infections, multiple sclerosis, Amyotrophic Lateral Sclerosis (ALS), cognitive impairment in depression, or post-operative cognitive dysfunction.

11. The method of claim 1, wherein applying the electromagnetic field to the subject through the at least one electromagnetic emitter in the array includes enhancing or reducing secretion of granulocyte colony-stimulating factor (GCSF) cytokine in cerebrospinal fluid (CSF).

12. The method of claim 11, wherein applying the electromagnetic field to the subject through the at least one electromagnetic emitter in the array includes at least one of:
increasing a number of microglial cells;
increasing or decreasing microglial cell activity in the brain;
increasing synapses in the brain; or
increasing a number of neurons in a hippocampus.

13. The method of claim 1, wherein the rebalancing of the brain-immune mediator levels in an area under the at least one electromagnetic emitter by applying the electromagnetic field to the subject through the at least one electromagnetic emitter includes periodic treatments at predetermined intervals.

14. The method of claim 1, wherein applying the electromagnetic field to the subject through the at least one electromagnetic emitter in the array includes treating immunological dysfunctions characterized by abnormal or unbalanced brain immune mediator levels.

15. The method of claim 1, wherein applying the electromagnetic field to the subject through the at least one electromagnetic emitter in the array regulates and coordinates cerebrospinal fluid (CSF) and peripheral immune system circulation to facilitate robust pro- and anti-inflammatory immune mediator components.

16. The method of claim 15, wherein applying the electromagnetic field to the subject through the at least one electromagnetic emitter in the array includes increasing modulation of the brain's meningeal lymphatic system by cytokines to provide such regulation and coordination between the CSF and peripheral immune system circulation.

17. The method of claim 1, further comprising applying TEMT to a head of the subject to increase flow through the brain's meningeal lymphatic system to enhance clearance of amyloid-beta (Aβ) and tau isoforms from the brain, along with brain toxins and metabolites.

* * * * *